United States Patent [19]

Cameron et al.

[11] Patent Number: 4,614,548
[45] Date of Patent: Sep. 30, 1986

[54] CHROMATOGRAPHIC SEPARATION OF DEXTROSE FROM STARCH HYDROLYSATE

[75] Inventors: Lawrence E. Cameron, Waterloo; Robert H. M. Stouffs, Brussels, both of Belgium

[73] Assignee: CPC International Inc., Englewood Cliffs, N.J.

[21] Appl. No.: 643,591

[22] Filed: Aug. 23, 1984

[30] Foreign Application Priority Data

Aug. 31, 1983 [GB] United Kingdom ............... 8323383

[51] Int. Cl.$^4$ .............................................. C13K 1/06
[52] U.S. Cl. ................................... 127/40; 127/46.2; 127/55; 210/656; 210/659; 210/663; 210/669; 435/96
[58] Field of Search ............... 210/659, 656, 663, 669; 127/36, 38, 40, 46.1, 46.2, 46.3, 55; 435/96

[56] References Cited

U.S. PATENT DOCUMENTS

| 3,756,919 | 9/1973 | Deaton | 127/40 |
| 3,817,787 | 6/1974 | Von Hertzen et al. | 127/46.2 X |
| 4,109,075 | 8/1978 | Deaton | 536/102 X |
| 4,133,696 | 1/1979 | Barker et al. | 127/46.2 |
| 4,206,284 | 6/1980 | Poulsen et al. | 435/96 |
| 4,266,027 | 5/1981 | Muller et al. | 127/46.1 X |
| 4,338,398 | 7/1982 | Yoneyama | 435/96 X |

FOREIGN PATENT DOCUMENTS 2302841 8/1973 Fed. Rep. of Germany ..... 127/46.2

OTHER PUBLICATIONS

"Immobilized Glucoamylase", (JP 58/43789, 3/14/83), Chemical Abstracts, vol. 99, p. 243, Jul. 1983.

Primary Examiner—Richard V. Fisher
Assistant Examiner—W. Gary Jones

[57] ABSTRACT

A process for chromatographic separation of dextrose from starch hydrolysate wherein the aqueous raffinate produced by contacting the starch hydrolysate with a chromatographic column or bed is treated with glucoamylase and recycled, at least in part, for use as an eluant for dextrose. An immobilized glucoamylase is used in the treatment to produce an aqueous dextrose-containing solution. It is this solution that is recycled and used, at least in part, as the eluant in the chromatographic column or bed used in the process.

18 Claims, No Drawings 4,614,548

CHROMATOGRAPHIC SEPARATION OF DEXTROSE FROM STARCH HYDROLYSATE

BACKGROUND OF THE INVENTION

1. Field of the Invention

The present invention relates to a process for hydrolysing starch to dextrose and particularly concerns an improved process for chromatographic separation of dextrose from starch hydrolysate.

2. The Prior Art

Processes for hydrolysing starch to dextrose have been known for many years and have been subject to a number of modifications and improvements. One aim has been to produce a dextrose product having very high purity either by converting as much of the starch as possible to dextrose to the exclusion of by-products or by providing an efficient method of separating the dextrose from such by-products.

One method of separation of the dextrose is by means of a chromatographic column or bed in which the aqueous starch hydrolysate, suitably after pretreatment such as concentration, filtration and/or decolorization, is absorbed on the column, the by-products passing through the column in the aqueous raffinate. The dextrose is then desorbed by elution with water and the water partially or completely removed to produce a concentrated solution or solid dextrose, the dextrose comprising more than 98% of the dry solids of the solution.

When the chromatographic method of separation is used the dextrose is produced together with the by-products in the aqueous raffinate. This raffinate may contain up to 20 wt % dry solids which may in turn be up to 80 wt % dextrose. The raffinate is usually recycled to an earlier stage in the process but such bulk recycle reduces the plant capacity. The present invention provides a solution to this problem and at the same time gives rise to additional process advantages.

DESCRIPTION OF THE INVENTION

According to the invention a process for the conversion of starch to dextrose is carried out as follows:

(a) hydrolysing an aqueous starch composition to a dextrose-containing product and separating dextrose from this product by (b) passing the product through a chromatographic column or bed to absorb dextrose on the column or bed and to produce an aqueous raffinate followed by (c) eluting the dextrose with water, in which the aqueous raffinate is (d) treated with an immobilized glucoamylase to produce an aqueous dextrose-containing solution which is used at least in part as the eluant for the chromatographic column or bed.

Stage (a) of the process is carried out in a conventional manner. Thus, the starch, which may be corn, wheat, potato or other form of starch, is gelatinized and thinned with acid or enzyme. The starch concentration is typically 20–45% dry substance and the enzyme a bacterial amylase preparation.

The thinned starch is hydrolysed, preferably at 45° to 60° C. and pH 3.0 to 4.5 using a glucoamylase enzyme. By this technique a hydrolysate containing dry solids comprising between 70 and 98% by weight dextrose is produced which is suitably filtered to remove traces of insoluble fat, protein and starch and is then preferably treated with powdered or granular carbon and/or ion-exchange resins to remove trace impurities, color and inorganic ash-forming contaminants. The dextrose solution is now in a suitable condition for concentration by means of the chromatographic treatment in stage (b). In addition to dextrose, the solution contains polysaccharides such as maltose, maltotriose and high polysaccharides.

The use of chromatography for the separation of dextrose and polysaccharides is in itself not new, for example, U.S. Pat. Nos. 3,817,787; 4,109,075; and 4,133,696 describe processes in which polysacchardide separations take place using a variety of techniques involving absorption and desorption from solid absorbents. The process may be one of exclusion chromatography which uses a column or bed of porous absorbent through which the dextrose solution is passed. The higher molecular weight polysaccharides, because of their greater molecular size, cannot diffuse into the pores of the absorbent and hence pass more quickly through the column or bed. Porous materials suitable for use in this form of exclusion chromatograph include ion-exchange resins, granulated forms of dextran, argarose and polyacrylamide gels, porous glass beads, activated carbon or alumina and controlled pore ceramics. Preferred absorbents for use in the chromatographic column or bed are ion exchange resins such as cation exchange resins, particularly metal salts of sulfonated cross-linked vinyl aromatic resins, e.g. the sodium or calcium form of a sulfonated cross-linked polystyrene resin. The cross-linking may be effected by means of divinyl benzene.

One or more columns or beds may be used in carrying out this stage of the process but for continuous operation of the process at least two columns or beds should be used, one being loaded while the other is being eluted. The column or bed is preferably maintained at a temperature in the range of 45° to 70° C. and the dextrose solution is passed through until the column is fully loaded and ready for elution.

In another form, particularly suited for commercial operation, the process is carried out continuously using a simulated moving bed of absorbent in which the bed is stationary and the movement is simulated by a programmed movement of feed and withdrawal points in the direction of liquid flow. In this form of the process, stage (d) is in the form of a closed loop in which aqueous raffinate withdrawn from the bed is treated with the immobilized glucoamylase and returned at least in part to the bed. The raffinate stream passing through the column or bed contains the polysaccharide constituents of the dextrose solution and varying amounts of dextrose, e.g. 2% to 20% by weight dry solids comprising 60–80 weight percent dextrose. In the prior art it is this stream that is recirculated back to an early stage in the process and used to thin the starch prior to hydrolysis, usually necessitating the use of highly dilute starch solutions, while the chromatographic column or bed loaded with dextrose was eluted with fresh water to give a dextrose-containing solution which was concentrated by evaporation.

In accordance with the present invention, part or all of the raffinate from the chromatographic column or bed is fed to a separate column or bed comprising immobilized glucoamylase which is so operated as to hydrolyse a significant proportion of the polysaccharides to dextrose so that the aqueous solution leaving the enzyme column or bed contains dry solids comprising 80 to 98% by weight dextrose and with, preferably, at least the same dextrose content as the dextrose content of the dry solids of the dextrose-containing product passed through the chromatographic column or bed in stage (b). The solution leaving the glucoamylase column or bed, optionally with the addition of water, is then used as eluant for the chromatographic column or bed loaded with dextrose. By operating in this manner the amount of fresh water required for elution of the chromatographic column is reduced to 10 to 25% of that required in the prior art operation.

The glucoamylase column or bed comprises glucoamylase supported on a solid support. The support should be porous and may be any support conventionally used for this purpose. Certain ion-exchange resins have been found to be very suitable, particularly, a porous weakly basic anion exchange resin of the phenolformaldehyde type is preferred. More than one such column or bed may be used in the process according to the invention.

The chromatographic column raffinate fed to the glucoamylase column or bed is first adjusted to a pH in the range 3 to 5, preferably about 3.5 by addition of a suitable acid, e.g. hydrochloric acid and 70 to 200 ppm sulfur dioxide may be added as sterilizing agent and pH buffer. The temperature of operation of the glucoamylase column or bed is from 45° to 75° C. preferably about 50° C. and the raffinate is passed through the column or bed at the rate required to produce the desired dextrose content of the dry solid component of the solution leaving the column or bed, based on a suitable enzyme loading on the bed of e.g. 20 units/ml carrier.

The solution leaving the glucoamylse column or bed may contain 1% to 19% by weight dry solids comprising 80 to 98 weight percent dextrose and may be used directly to elute the chromatographic column or bed optionally after purification, such as by filtration and/or decolorization, or may be stored until required for this purpose. The elution may for example take place at a temperature of 45° to 70° C. and produces an eluate containing 80 to 98 weight % dextrose. This dextrose solution may be concentrated by evaporation and on a dry solid basis may comprise more than 98% by weight dextrose.

If desired, a part of the chromatographic column raffinate may be bled-off either before or after the glucoamylase column or bed. This technique may be used if it is suspected that there is a build-up of by-products in the solution used to elute the chromatographic column. The solution bled-off in this way may be recycled to an earlier stage in the process, e.g. to stage (a).

EXAMPLES

The invention will now be further described with reference to the following Examples:

EXAMPLE 1

Stage (a)

An enzyme thinned corn starch solution comprising 30% by weight dry substance was hydrolysed by mixing with a glucoamylase enzyme at a pH of 3.5 and at a temperature of 50° C.

Stage (b)

The solution produced in (a) contained 32-33% by weight dry solids of which 95.5% was dextrose, the remainder being maltose, maltotriose and higher polysacchardides containing 4, 5 and more dextrose units. This solution was filtered through diatomaceous earth in a rotary vacuum filter, treated with decolorizing carbon and passed through two pairs of cation/anion exchange beds. The solution was finally evaporated to 60% by weight dry substance content. The pH of the filtered, decolorized and de-ashed solution was adjusted to 4 and the solution was fed continuously to a simulated moving bed packed with the sodium form of a cation exchange resin at a temperature of 60° C. to 65° C. Dextrose was absorbed on the bed and the raffinate solution leaving the bed contained 2% by weight dry solids comprising 67.9% dextrose, 10.5% maltose, 1.6% maltulose, 8.4% isomaltose, 3% maltotriose and 8.6% higher polysaccharides, all percentages being by weight.

Stage (d)

The raffinate solution from the chromatographic bed was hydrolysed in a glucoamylase column comprising glucoamylase supported on a porous weakly basic anion exchange resin of the phenol/formaldehyde type (DUOLITE ES-568 produced by Diamond Shamrock) the enzyme loading being 20 units/ml support. The raffinate solution was first adjusted to pH 3.5 by addition of hydrochloric acid and some 150 ppm sulfur dioxide added before the solution was fed to the column. The column was operated at 50° C. and the flow rate of raffinate solution fed continuously to the column was 0.17 bed volume/hour. The product obtained after 3 days of continuous operation had a dry solid composition of 95.5% dextrose, 0.5% maltose, 1.0% maltulose, 1.1% isomaltulose, 0.4% maltotriose and 1.5% higher polysaccharides, all percentages being by weight.

After 10 days of continuous operation the product still contained 94.5% by weight dextrose when the flow rate was increased to 0.30 bed volume/hour.

Stage (c)

The solution produced in stage (d) was a suitable eluant for the chromatographic bed in stage (b), the eluate being a dextrose solution comprising dry solids containing more than 99% dextrose.

EXAMPLE 2

Example 1 was repeated except that the raffinate solution from the chromatographic bed contained 20% dissolved solids of which 67.9% by weight was dextrose.

At a feed rate of 0.25 bed volume/hour of this solution to the glucoamylase column a product was obtained which consisted of 85.1% dextrose, 1.6% maltose, 2.2% maltulose, 8.6% isomaltose, 1.2% maltotriose and 1.3% higher polysaccharides, all percentages being by weight.

After 8 days of operation at 20% dry solids, the dry solids of the raffinate solution to the glucoamylse column was reduced to 15%. At a flow rate of 0.50 bed volume/hour the column produced a solution which had a dry solid content containing 86% dextrose.

Having set forth the general nature and some examples of the present invention, the scope is now particularly set forth in the appended claims.

What is claimed is:

1. A process for converting starch to dextrose comprising
   (a) hydrolysing an aqueous starch composition to a dextrose-containing starch hydrolysate;
   (b) contacting said starch hydrolysate with a chromatographic column or bed to absorb dextrose on said column or bed and to produce an aqueous raffinate;

(c) eluting the dextrose with water; and (d) contacting the aqueous raffinate with an immobilized glucoamylase to produce an aqueous dextrose-containing solution, which is recycled, at least in part, and used as the eluant for said chromatographic column or bed.

2. The process of claim 1 wherein hydrolysis is carried out at 45° to 60° C. at a pH of 3.0 to 4.5 using a glucoamylse enzyme.

3. The process of claim 1 wherein the starch hydrolysate is filtered before it is contacted with said chromatographic column or bed.

4. The process of claim 1 wherein said chromatographic column or bed comprises a metal salt of a sulfonated cross-linked vinyl aromatic resin.

5. The process of claim 1 wherein said chromatographic column or bed is maintained at a temperature in the range of 45° to 70° C.

6. The process of claim 1 wherein said aqueous raffinate comprises 2% to 20% by weight dry solids, said dry solids comprising 60% to 80% by weight dextrose.

7. The process of claim 1 wherein said immobilized glucoamylase is immobilized on a porous, weakly-basic, anion exchange resin of the phenol-formaldehyde type.

8. The process of claim 1 wherein said aqueous raffinate fed to said immobilized glucoamylase is adjusted to a pH in range of 3 to 5.

9. The process of claim 1 wherein said aqueous raffinate is contacted with said immobilized glucoamylase at a temperature in the range of 45° to 75° C.

10. The process of claim 1 wherein said aqueous raffinate is contacted with said immobilized glucoamylase to produce a solution containing 1% to 19% dry solids, said dry solids comprising 80 to 98 weight % dextrose.

11. The process of claim 1 wherein said dextrose-containing solution is filtered before being used as eluant.

12. The process of claim 1 wherein the dextrose is eluted from the chromatographic column or bed at a temperature in the range of 45° to 70° C.

13. The process of claim 1 wherein the dextrose solution eluted from the chromatographic column or bed contains dry solids comprising more than 98% by weight dextrose.

14. The process of claim 1 wherein the starch hydrolysate is filtered and treated with powdered or granula carbon before it is contacted with said chromatographic column or bed.

15. The process of claim 1 wherein the starch hydrolysate is filtered and treated with ion exchange resins before it is contacted with said chromatographic column or bed.

16. The process of claim 1 wherein the starch hydrolysate is filtered and treated with powdered or granular carbon and ion exchange resins before it is contacted with said chromatographic column or bed.

17. The process of claim 1 wherein said dextrose-containing solution is decolorized before being used as eluant.

18. The process of claim 1 wherein said dextrose-containing solution is filtered and decolorized before being used as eluant.

* * * * *